United States Patent [19]

Inaba et al.

[11] Patent Number: 5,250,707
[45] Date of Patent: Oct. 5, 1993

[54] PROCESS FOR PREPARING ε-CAPROLACTONE

[75] Inventors: Yukio Inaba; Yohsuke Ueno; Takafumi Hirakawa; Suzuo Takiguchi, all of Ube, Japan

[73] Assignee: Ube Industries, Ltd., Ube, Japan

[21] Appl. No.: 689,151

[22] Filed: Apr. 22, 1991

[30] Foreign Application Priority Data

Apr. 25, 1990 [JP] Japan .................. 2-107674

[51] Int. Cl.⁵ .......................... C07D 313/04
[52] U.S. Cl. .................................. 549/266
[58] Field of Search ........................ 549/266

[56] References Cited

U.S. PATENT DOCUMENTS

| | | | |
|---|---|---|---|
| 2,914,556 | 11/1959 | Hostettler et al. | 549/266 |
| 3,064,008 | 11/1962 | Phillips et al. | 549/266 |
| 3,189,619 | 6/1965 | Aldridge et al. | 549/266 |
| 3,317,563 | 5/1967 | Horlenko et al. | 549/266 |
| 3,523,955 | 11/1970 | Lantz et al. | 549/266 |
| 3,624,258 | 11/1971 | Ishimoto et al. | 549/266 |
| 3,766,212 | 7/1971 | Waldmann et al. | 549/266 |
| 3,781,350 | 12/1973 | Fujita et al. | 549/266 |
| 3,825,570 | 7/1974 | Fujita et al. | 549/266 |
| 4,183,863 | 1/1980 | Higley et al. | 549/266 |

FOREIGN PATENT DOCUMENTS

| | | |
|---|---|---|
| 0084286 | 7/1983 | European Pat. Off. . |
| 0349861 | 1/1990 | European Pat. Off. . |
| 0204184 | 11/1984 | Japan . |
| 1200120 | 9/1986 | Japan . |
| 1140184 | 1/1969 | United Kingdom . |
| 1153364 | 5/1969 | United Kingdom . |

Primary Examiner—C. Warren Ivy
Assistant Examiner—A. A. Owens
Attorney, Agent, or Firm—Frishauf, Holtz, Goodman & Woodward

[57] ABSTRACT

Disclosed is a process for preparing ε-caprolactone comprising using a percarboxylic acid solution obtained by oxidizing organic carboxylic acid in an organic solvent in the presence of hydrogen peroxide and a boric acid catalyst, and cyclohexanone, supplying 1 to 1.5 mole of percarboxylic acid, 0.012 mole or less of hydrogen peroxide and 0.04 mole or less of the boric acid catalyst per mole of cyclohexanone in a reaction system, and reacting said cyclohexanone with said percarboxylic acid to form ε-caprolactone.

14 Claims, 1 Drawing Sheet

PROCESS FOR PREPARING ε-CAPROLACTONE

BACKGROUND OF THE INVENTION

This invention relates to a process for forming ε-caprolactone effectively (with high yield) while substantially inhibiting formation of by-products by supplying a percarboxylic acid solution obtained by oxidizing organic carboxylic acids in an organic solvent in the presence of hydrogen peroxide and a boric acid catalyst, and cyclohexanone in a reaction system so that the rates of hydrogen peroxide and the boric acid catalyst formulated are smaller, and effecting an oxidation reaction of cyclohexanone with percarboxylic acid in the reaction system.

Since a reaction mixture containing the ε-caprolactone obtained as described above contains substantially no by-product which is difficult to be separated and purified, ε-caprolactone having high purity can be obtained easily by a conventional purification process such as a distillation process.

In the prior art, it has been known that ε-caprolactone is prepared by reacting cyclohexanone with a percarboxylic acid such as peracetic acid and perpropionic acid (Baeyer-Villiger oxidation reaction). However, in the conventional preparation process, since various by-products such as adipic acid and 5-hexenoic acid are formed, it is extremely difficult to perform purification for isolating ε-caprolactone having high purity from a reaction mixture containing ε-caprolactone, and ε-caprolactone containing such by-products has exerted bad influence on production of polymers such as polyesterol and polyurethane.

As a purification process for isolating ε-caprolactone from a reaction mixture containing ε-caprolactone obtained by the above preparation process, there have been proposed various techniques, for example, (1) a process in which low boiling point components of crude ε-caprolactone prepared by reacting cyclohexanone with a percarboxylic acid solution are distilled by a first distillation device, and then a product is distilled out by a second distillation device (Japanese Unexamined Patent Publication No. 34677/1981 and Japanese Unexamined Patent Publication No. 42684/1982).

(2) a process in which low boiling point components are removed by distillation from a reaction mixture obtained by oxidizing cyclohexanone, and then inert gas is introduced into a condenser of a second distillation column to prevent condensation of water (Japanese Patent Publication No. 59238/1985) and (3) a process in which crude ε-caprolactone is treated with an acidic sulfite type anion exchange resin (Japanese Patent Publication No. 16437/1985). However, since these techniques require complicated purification steps or frequently form by-products (impurities) which cannot be separated by a purification operation such as a distillation operation in the above preparation process, there is a problem that they cannot be applied to a reaction mixture containing ε-caprolactone containing such impurities.

In recent years, there has been proposed a process in which in preparation of a percarboxylic acid to be used for oxidation reaction of cyclohexanone, a boric acid catalyst forming small amounts of by-products in preparation of ε-caprolactone is used in place of a strongly acidic catalyst such as sulfuric acid, and a percarboxylic acid solution obtained as a result is used as such for preparation of ε-caprolactone. Specifically, in Japanese Unexamined Patent Publication No. 150681/1982 and Japanese Unexamined Patent Publication No. 124781/1983, there has been proposed a process in which in preparation of stable ε-caprolactone by oxidizing cyclohexanone with percarboxylic acid having 2 to 4 carbon atoms, corresponding carboxylic acid and hydrogen peroxide are used in the form of a "crude solution of percarboxylic acid" obtained by reacting them in the presence of a boric acid catalyst and also while removing water continuously under azeotropic condition to prepare a stable ε-caprolactone solution. In this conventional process, since weak acid such as boric acid is used, smaller amounts of by-products are formed in preparation of ε-caprolactone when compared with the case where a strongly acidic catalyst is used, but a large amount of low boiling point components such as oxycaproic acid and high boiling point components such as an oligomer of 1,4-caprolactone, 5-hexenoic acid, ethyl propionicoxycaproate and ethyl oxycaproate are still formed as a by-product, whereby the process is not sufficiently satisfactory.

Accordingly, for preparing ε-caprolactone industrially by using percarboxylic acid and cyclohexanone, a preparation process which can inhibit substantially sufficiently amounts of by-products formed which are undesirable products in purification (impurities such as the low boiling point components and high boiling point components as described above) has been expected strongly.

SUMMARY OF THE INVENTION

An object of the present invention is to provide an industrial process which can prepare ε-caprolactone with high yield without forming by-products (impurities) which are difficult to be separated by purification such as distillation.

The present invention relates to a process for preparing ε-caprolactone comprising using a percarboxylic acid solution obtained by oxidizing organic carboxylic acid in an organic solvent in the presence of hydrogen peroxide and a boric acid catalyst, and cyclohexanone, supplying 1 to 1.5 mole of percarboxylic acid, 0.012 mole or less of hydrogen peroxide and 0.04 mole or less of the boric acid catalyst per mole of cyclohexanone in a reaction system, and reacting said cyclohexanone with said percarboxylic acid in the reaction system to form ε-caprolactone.

DESCRIPTION OF THE PREFERRED EMBODIMENTS

Figure 1:
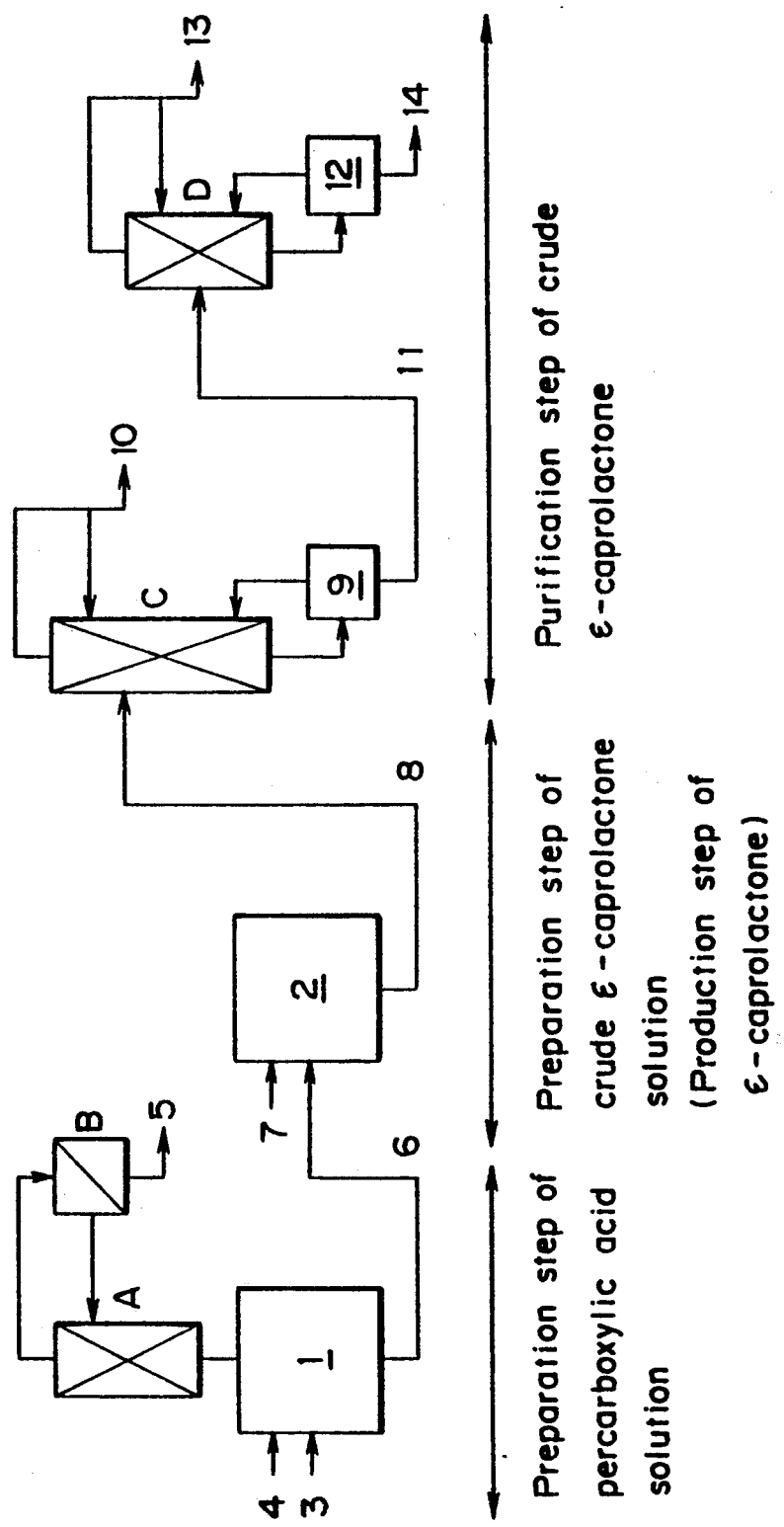
FIG. 1 shows one example of a preparation flow comprising a step for preparing a percarboxylic acid solution, a step for forming ε-caprolactone (a step for preparing a crude ε-caprolactone solution) and a step for purifying a crude ε-caprolactone solution, which can be used for practicing the present invention, wherein 1 is a glass reactor, 2 is a reactor, 9 is a reboiler, 12 is a reboiler, A is a distillation column, B is a reflux condenser with a settler, C is a distillation column and D is a distillation column.

In the following, important points of the present invention are described in more detail.

In the preparation process of the present invention, first, the percarboxylic acid solution and cyclohexanone described above are used and supplied in an "oxidation reaction system of cyclohexanone" so that (a) the rate of the percarboxylic acid used is 1 to 1.5 mole, preferably about 1.05 to 1.4 mole, particularly about 1.1 to 1.3 mole per mole of the above cyclohexanone, (b) the rate of hydrogen peroxide used is as low as 0.012 mole or less (preferably about 0.001 to 0.01 mole) per mole of the above cyclohexanone, and (c) the rate of the boric acid catalyst used (calculated on orthoboric acid) is as low as 0.04 mole or less (preferably 0.001 to 0.03 mole, more preferably 0.005 to 0.018 mole) per mole of the above cyclohexanone.

If the used amount of percarboxylic acid is less than 1 mole per mole of cyclohexanone and exceeds 1.5 mole per mole of cyclohexanone, the by-products are increased. Further, if the used amount of hydrogen peroxide and a boric acid catalyst exceeds the above-defined amount, the by-products are also increased.

The "cyclohexanone" to be used in the preparation process of the present invention may be a compound substantially containing neither impurity which is difficult to be separated in purification of $\epsilon$-caprolactone nor precursor thereof, preferably a compound having high purity comprising 95% by weight or more, particularly 98% by weight or more of cyclohexanone.

In the preparation process of the present invention, in the "oxidation reaction system of cyclohexanone", a small amount of a stabilizer such as a phosphate, a phosphate ester, picolinic acid, dipicolinic acid and pyridine derivatives including picoline and lutidine which can inhibit loss caused by decomposition of percarboxylic acid due to a minute amount of metal is preferably contained.

The above "percarboxylic acid solution" to be used in the preparation process of the present invention is a solution of percarboxylic acid such as peracetic acid, perpropionic acid and perbutyric acid obtained by oxidizing organic carboxylic acid in an organic solvent in the presence of hydrogen peroxide and a boric acid catalyst.

It is preferred that in the above percarboxylic acid solution, the rate of percarboxylic acid formed by oxidizing organic carboxylic acid such as acetic acid, propionic acid and butyric acid contained is 5 to 40% by weight, particularly 10 to 30% by weight, the rate of hydrogen peroxide contained is as low as about 0.01 mole or less, particularly about 0.001 to 0.008 mole per mole of the above percarboxylic acid, and further the rate of a boric acid catalyst contained (calculated on orthoboric acid) is as low as 0.03 mole or less, particularly about 0.005 to 0.02 mole per mole of the above percarboxylic acid. Thus, the respective components can be mixed at the mixing rates described above, and therefore a mixture to be used for an oxidation reaction of cyclohexanone can be prepared easily.

In the above percarboxylic acid solution, 10 to 70% by weight, particularly 20 to 65% by weight of organic carboxylic acid may be contained, and further 5 to 60% by weight, particularly 10 to 55% by weight of an organic solvent may be contained.

As the above organic carboxylic acid, preferred is aliphatic carboxylic acid, and most preferred is propionic acid from which perpropionic acid to be suitably used for oxidation of cyclohexanone can be obtained.

As the above organic solvent, there may be mentioned aliphatic carboxylic acid lower alkyl ester derived from saturated aliphatic monovalent alcohol having 1 to 5 carbon atoms such as methanol, ethanol, 1-propanol, iso-propanol, 1-butanol, iso-butanol and 1-pentanol, and aliphatic carboxylic acid such as acetic acid, propionic acid and butyric acid, particularly preferably propionic acid lower alkyl ester (e.g. ethyl propionate) derived from lower alcohol having 1 to 3 carbon atoms and propionic acid.

As the above boric acid catalyst, there may be mentioned orthoboric acid and metaboric acid.

As a process for preparing the above percarboxylic acid solution to be used for the preparation process of the present invention, there may be preferably mentioned an industrial process for preparing the "percarboxylic acid solution having the above composition", in which an organic carboxylic acid such as propionic acid, and hydrogen peroxide are reacted in an organic solvent such as propionic acid lower alkyl ester which can form a heterogeneous azeotrope together with water, in the presence of a boric acid catalyst such as orthoboric acid and metaboric acid at a temperature of 30° to 100° C., particularly 50° to 80° C., and percarboxylic acid such as perpropionic acid is formed while removing water introduced together with hydrogen peroxide during progress of the reaction and reaction water formed during the reaction continuously by azeotropic distillation using an azeotropic distillation column equipped with a condenser and a decanter.

As described above, the "percarboxylic acid solution containing small amounts of hydrogen peroxide and boric acid" which can be suitably used in the preparation process of the present invention can be obtained easily, and a reaction mixture containing perpropionic acid can be used such as for the next oxidation reaction of cyclohexanone without purifying the percarboxylic acid solution.

In the process for preparing the above percarboxylic acid solution, hydrogen peroxide is preferably supplied in the form of an aqueous solution comprising 30 to 70% by weight of hydrogen peroxide. The molar ratio of the organic carboxylic acid to hydrogen peroxide to be used is not particularly limited, but for reacting hydrogen peroxide effectively, the molar ratio of the organic carboxylic acid to hydrogen peroxide (organic carboxyic acid/hydrogen peroxide) used in the first place is desirably 1.4 to 6, particularly 1.5 to 5. Further, the amount of the catalyst to be added is desirably 0.03 mole or less, particularly about 0.005 to 0.02 mole per mole of hydrogen peroxide supplied in the reaction system in the first place.

In preparation of the above percarboxylic acid solution, the amount of the organic solvent such as carboxylic acid alkyl ester to be used is desirably 0.3 to 15 times in terms of weight based on the total amount of water introduced together with hydrogen peroxide and water formed during the reaction for effective azeotropic distillation of water existing in the reaction system.

Further, in preparation of the above percarboxylic acid solution, as a process for removing water formed during the reaction, there may be mentioned, for example, a process in which the above organic solvent and water are distilled azeotropically in an azeotropic distillation column equipped with a condenser and a decanter, a distillate condensed by a condenser is introduced into a decanter and separated by decantation into an organic phase and an aqueous phase, only the organic phase is refluxed to an azeotropic distillation column and the aqueous phase is drawn continuously, and azeotropic dehydration is continued until the above distillate introduced into a decanter will not substantially be separated into an organic phase and an aqueous phase.

In preparation of the above percarboxylic acid solution, the reaction pressure can be varied depending on a composition of the reaction system and a temperature selected, but preferably a reduced pressure of 10 to 300 mmHg.

In the preparation process of the present invention, it is preferred that ϵ-caprolactone is prepared effectively by using the mixture for an oxidation reaction of cyclohexanone prepared as described above, and oxidizing cyclohexanone in the mixture with the above percarboxylic acid at a reaction temperature of 30° to 80° C., particularly preferably in the range of 40° to 70° C. and for a reaction time of 1 to 8 hours, particularly preferably in the range of 2 to 5 hours to form ϵ-caprolactone.

If the above reaction time is too long, a reaction in which a by-product undesirable in purification of ϵ-caprolactone is formed is caused unnegligibly, whereby deterioration of yield of ϵ-caprolactone and increase in formation of impurities are brought about undesirably.

According to the preparation process of the present invention, ϵ-caprolactone can be prepared with good reproducibility and with high yield, i.e. with a conversion of 97% or more based on cyclohexanone used in an oxidation reaction, a selectivity of 99% or more based on cyclohexanone consumed and a selectivity of 99.5% or more based on percarboxylic acid consumed, and ϵ-caprolactone containing extremely small amounts of by-products (impurities) formed can be obtained.

The purification step for isolating ϵ-caprolactone from an oxidation reaction mixture obtained by the preparation process of the present invention can be carried out by using a "crude ϵ-caprolactone solution (oxidation reaction mixture)" obtained in the above "step for oxidizing cyclohexanone" according to a conventional distillation process.

The above distillation process can be performed by, for example, removing a process in which low boiling point components such as percarboxylic acid, carboxylic acid and carboxylic acid alkyl ester, and then distilling ϵ-caprolactone out by a second distillation column. For reducing loss caused by decomposition of peroxide and also inhibiting pyrolysis of ϵ-caprolactone, this process is preferably performed under a reduced pressure of about 1 to 100 mmHg. In the above distillation process, as a distillation device, there may be desirably used a device of a type which is suitable for distillating a substance sensitive to heat, such as a thin layer evaporator and a falling film evaporator.

Thus, since the oxidation reaction mixture obtained by the preparation process of the present invention contains extremely small amounts of by-products in oxidation reaction, ϵ-caprolactone having high purity can be obtained easily by purifying the oxidation reaction mixture by the above distillation method under reduced pressure substantially without causing decomposition by distillation.

Further, in the preparation process of the present invention, ϵ-caprolactone can be prepared either continuously or batchwise.

EXAMPLES

The present invention is described in detail by referring to Examples and Comparative examples.

In the respective Examples and Comparative examples, the concentrations of hydrogen peroxide and perpropionic acid were determined according "cerium sulfate titration" and "thiosulfate titration", respectively, and the amounts of ϵ-caprolactone, propionic acid and ethyl propionate were quantitated by gas chromatography.

EXAMPLE 1

Mostly according to a preparation flow as shown in FIG. 1, ϵ-caprolactone was prepared.

Preparation of perpropionic acid solution

Into a glass reactor 1 having a volume of 2 liters equipped with a distillation column A with 20 sheets of Oldershaw plates and a reflux condenser B with a settler, a solution comprising:

| Propionic acid | 504 g |
|---|---|
| Ethyl propionate | 126 g |
| Orthoboric acid | 1.6 g |
| 2-Picoline (stabilizer) | 0.6 g | was charged from a supply line 3.

Next, the reactor 1 was immersed in an oil bath and heated to 100° C. whereby this solution was heated up to a boiling point while refluxing under a reduced pressure of 60 mmHg and stirring, and 60% by weight of hydrogen peroxide was added over 30 minutes from a supply line 4 in a total amount of 107.4 g. The temperature of the reactor 1 was about 65° C., and an organic phase in which hetero azeotropic substances were condensed was recirculated from the reflux condenser B with a settler to maintain generation of reflux. On the other hand, an aqueous phase condensed was drawn continuously from a draw line 5 of the reflux condenser B with a settler. After propionic acid and hydrogen peroxide were reacted until the aqueous phase was not substantially separated by the reflux condenser B with a settler as described above, heating of the reactor 1 was stopped to terminate the reaction. Thus, 686.7 g of a perpropionic acid solution was prepared. The reaction required 4 hours from the starting point of the addition of hydrogen peroxide.

The perpropionic acid solution obtained from a bottom of the reactor 1 had the following composition (% by weight).

| Ethyl propionate | 18.4% |
|---|---|
| Propionic acid | 57.7% |
| Perpropionic acid | 23.5% |
| Hydrogen peroxide | 0.05% |
| Orthoboric acid | 0.23% |

The conversion of hydrogen peroxide was 99.5%, and the selectivity to perpropionic aid was 95.0%.

Preparation of crude ϵ-caprolactone solution

Next, in a glass reactor 2 having a volume of 1 litter equipped with a reflux condenser and with a jacket connected to a heat transfer medium circulating tank (not shown) so designed that the temperature of a reaction mixture could be controlled, 650 g of the percarboxylic acid solution obtained as described above (perpropionic acid: 1.70 mole) was charged through a supply line 6.

Subsequently, the perpropionic acid solution in this reactor 2 was heated to 50° C. while stirring, and a total amount of 138.7 g (1.414 mole) of cyclohexanone was added over 30 minutes from a supply line 7. After the mixture was reacted as such for 3 hours from the starting point of the addition of cyclohexanone while maintaining its temperature at 50° C., the mixture was cooled to room temperature to prepare 786.3 g of a crude ε-caprolactone solution.

The crude ε-caprolactone solution obtained had the following composition (% by weight).

| | |
|---|---|
| Ethyl propionate | 15.1% |
| Propionic acid | 60.7% |
| ε-Caprolactone | 20.1% |
| Perpropionic acid | 3.5% |
| Hydrogen peroxide | 0.01% |
| Cyclohexanone | 0.33% |
| Orthoboric acid | 0.16% |

The conversion of cyclohexanone was 98.1%, and the selectivity to ε-caprolactone was 99.8%. The conversion of perpropionic acid was 82.1%, and the selectivity to ε-caprolactone was 99.5%.

Purification of crude ε-caprolactone solution

Into a distillation column C operated under a pressure of 10 mmHg and equipped with a thin layer evaporator as a reboiler 9 (height of filler: 495 mm), this crude ε-caprolactone solution was charged continuously at a rate of 260 g/hour through a supply line 8.

Low boiling point components were drawn from a draw line 10 of the distillation column C at a rate of 207.1 g/hour while refluxing at a reflux rate of 0.25, and crude ε-caprolactone concentrated was drawn from a bottom of the distillation column C at a rate of 52.9 g/hour.

Further, into a distillation column D operated under a pressure of 10 mmHg and equipped with a thin layer evaporator (with 10 sheets of Oldershaw plates) as a reboiler 12, the crude ε-caprolactone was charged continuously at a rate of 75 g/hour from a supply line 11.

In the distillation column D, ε-caprolactone was drawn continuously at a rate of 72.0 g/hour from a draw line 13 while refluxing at a reflux rate of 0.2, and high boiling point components were drawn from a draw line 14 at a lower part of the reboiler 12.

The purity of the ε-caprolactone obtained by this operation was 99.9% by weight (total amount of the low boiling point components such as δ-valerolactone and oxycaproic acid: 0.04% by weight or less, total amount of the high boiling point components such as 5-hexenoic acid, ethyl propionoxy caproate and ethyl oxycaproate: 0.05% by weight or less), which was a satisfactory product purity.

EXAMPLE 2 (COMPARATIVE EXAMPLE 1)

670.4 g of a perpropionic acid solution was prepared in the same manner as in Example 1 except for changing the amount of orthoboric acid used from 1.6 g to 6.4 g. The reaction required 2.5 hours from the starting point of addition of hydrogen peroxide.

The perpropionic acid solution obtained had the following composition (% by weight).

| | |
|---|---|
| Ethyl propionate | 19.8% |
| Propionic acid | 54.7% |

-continued

| | |
|---|---|
| Perpropionic acid | 24.2% |
| Hydrogen peroxide | 0.10% |
| Orthoboric acid | 0.95% |

The conversion of hydrogen peroxide was 99.0%, and the selectivity to perpropionic acid was 96.0%.

Next, a crude ε-caprolactone solution was prepared in the same manner as in Example 1 except for using 632.8 g of the percarboxylic acid solution obtained (perpropionic acid: 1.70 mole) and 139.0 g (1.417 mole) of cyclohexanone. The weight of the crude ε-caprolactone solution obtained was 767.1 g, and had the following composition (% by weight).

| | |
|---|---|
| Ethyl propionate | 16.4% |
| Propionic acid | 58.6% |
| ε-Caprolactone | 19.5% |
| Perpropionic acid | 3.6% |
| Hydrogen peroxide | 0.01% |
| Cyclohexanone | 0.36% |
| Orthoboric acid | 0.79% |

The conversion of cyclohexanone was 98.0%, and the selectivity to ε-caprolactone was 94.6%. The conversion of perpropionic acid was 81.8%, and the selectivity to ε-caprolactone was 94.2%.

Further, this crude ε-caprolactone solution was purified in the same manner as in Example 1 to obtain ε-caprolactone.

The purity of the ε-caprolactone was 99.6% by weight (the low boiling point components: about 0.08% by weight, the high boiling point components: about 0.25% by weight), which was not a satisfactory product purity.

EXAMPLE 3 (COMPARATIVE EXAMPLE 2)

680.1 g of a perpropionic acid solution was prepared in the same manner as in Example 1 except for changing the reaction time in preparation of the perpropionic acid solution to 3 hours and 15 minutes. At the time of terminating the above reaction, in the reflux condenser B with a settler, an aqueous phase was still separated slightly from the draw line.

The perpropionic acid solution obtained from the bottom of the reactor 1 had the following composition (% by weight).

| | |
|---|---|
| Ethyl propionate | 18.4 % |
| Propionic acid | 57.7% |
| Perpropionic acid | 22.8% |
| Hydrogen peroxide | 0.43% |
| Orthoboric acid | 0.24% |

The conversion of hydrogen peroxide was 95.5%, and the selectivity to peropropionic acid was 95.3%.

Next, a crude ε-caprolactone solution was prepared in the same manner as in Example 1 except for using 651.9 g of the above percarboxylic acid solution (perpropionic acid: 1.65 mole) and 134.9 g (1.375 mole) of cyclohexanone. The weight of the crude ε-caprolactone solution obtained was 783.3 g, and had the following composition (% by weight):

| | |
|---|---|
| Ethyl propionate | 16.4% |
| Propionic acid | 58.6% |
| ε-Caprolactone | 18.9% |

| -continued | |
|---|---|
| Perpropionic acid | 4.5% |
| Hydrogen peroxide | 0.03% |
| Cyclohexanone | 0.17% |
| Orthoboric acid | 0.19% |

The conversion of cyclohexanone was 99.0%, and the selectivity to ε-caprolactone was 95.3%. The conversion of perpropionic acid was 76.3%.

Further, this crude ε-caprolactone solution was purified in the same manner as in Example 1 to obtain ε-caprolactone. The purity of the ε-caprolactone was 99.2% by weight (the low boiling point components: 0.35% by weight, the high boiling point components: about 0.35% by weight), which was not a satisfactory product purity.

As described above, the preparation process of the present invention is an excellent industrial process for preparing ε-caprolactone with high yield while inhibiting formation of by-products (impurities) which become a problem in purification, by limiting the rate of percarboxylic acid to be mixed based on cyclohexanone within a specific range, preparing a mixture for reaction by mixing cyclohexanone and a percarboxylic acid solution by controlling so that the rate of hydrogen peroxide and the rate of a boric acid catalyst mixed based on cyclohexanone are smaller, and reacting cyclohexanone with percarboxylic acid in the mixture, and from the oxidation reaction mixture obtained as a result, ε-caprolactone having a purity of at least 99.8% by weight can be obtained easily.

We claim:

1. In a process for preparing ε-caprolactone comprising;
   i) preparing a percarboxylic acid solution mixture by
      (a) oxidizing organic carboxylic acid in a reaction mixture including an organic solvent comprising a lower alkyl ester of an aliphatic carboxylic acid, in the presence of hydrogen peroxide and boric acid catalyst,
      (b) while removing water from the reaction mixture by distillation as an azeotrope which includes said organic solvent,
   ii) supplying the percarboxylic acid solution mixture and cyclohexanone to the reaction system for reacting cyclohexanone with the percarboxylic acid, to prepare a reaction-starting mixture in which
      (a) the rate of the percarboxylic acid supplied is 1 to 1.5 mole per mole of the cyclohexanone,
      (b) the rate of hydrogen peroxide supplied with the percarboxylic acid is 0.001 to 0.01 mole per mole of the cyclohexanone, and
      (c) the rate of the boric acid catalyst supplied with the percarboxylic acid is 0.001 to 0.03 mole per mole of the cyclohexanone, and then,
   iii) reacting the cyclohexanone with percarboxylic acid in the reaction system, so as to synthesize ε-caprolactone with high yield and purity and to inhibit side reactions.

2. The process of claim 1 wherein the used amount of said percarboxylic acid is about 1.05 to 1.4 mole per mole of said cyclohexanone.

3. The process of claim 2 wherein the used amount of said percarboxylic acid is about 1.1 to 1.3 mole per mole of said cyclohexanone.

4. The process of claim 1 wherein the used amount of said boric acid catalyst is 0.005 to 0.018 mole per mole of said cyclohexanone.

5. The process of claim 1 wherein the reaction temperature is in the range of 30° to 80° C.

6. The process of claim 5 wherein the reaction temperature is in the range of 40° to 70° C.

7. The process of claim 1 wherein the reaction time is in the range of 1 to 8 hours.

8. The process of claim 7 wherein the reaction time is in the range of 2 to 5 hours.

9. The process of claim 1 wherein said percarboxylic acid is perpropionic acid.

10. The process of claim 7 wherein the reaction further contains a stabilizer.

11. The process of claim 10 wherein said stabilizer is at least one compound selected from the group consisting of a phosphate, a phosphate ester, picolinic acid, dipicolinic acid, picoline and lutidine.

12. The process of claim 1, wherein the reaction temperature is 30° C. to 80° C., and the reaction time is 1 to 8 hours.

13. The process of claim 1 wherein said organic solvent is a lower alkyl ester of propionic acid.

14. The process of claim 1 wherein said organic solvent is ethyl propionate.

* * * * *